United States Patent
Rangnekar et al.

(10) Patent No.: US 11,730,750 B2
(45) Date of Patent: *Aug. 22, 2023

(54) DRUGS FOR GRP78 CELL SURFACE TRANSLOCATION AND PAR-4 SECRETION

(71) Applicant: University of Kentucky Research Foundation, Lexington, KY (US)

(72) Inventors: Vivek M. Rangnekar, Nicholasville, KY (US); Ravshan Burikhanov, Lexington, KY (US); David S. Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/178,096

(22) Filed: Feb. 17, 2021

(65) Prior Publication Data

US 2021/0252032 A1 Aug. 19, 2021

Related U.S. Application Data

(60) Provisional application No. 62/977,582, filed on Feb. 17, 2020.

(51) Int. Cl.
| | | |
|---|---|---|
| *A61K 31/7048* | (2006.01) | |
| *A61K 45/06* | (2006.01) | |
| *A61K 31/4706* | (2006.01) | |
| *A61K 31/704* | (2006.01) | |
| *A61K 31/55* | (2006.01) | |
| *A61K 31/4545* | (2006.01) | |
| *A61K 31/675* | (2006.01) | |
| *A61K 31/497* | (2006.01) | |
| *A61K 31/517* | (2006.01) | |
| *A61K 31/4745* | (2006.01) | |

(52) U.S. Cl.
CPC ...... *A61K 31/7048* (2013.01); *A61K 31/4545* (2013.01); *A61K 31/4706* (2013.01); *A61K 31/4745* (2013.01); *A61K 31/497* (2013.01); *A61K 31/517* (2013.01); *A61K 31/55* (2013.01); *A61K 31/675* (2013.01); *A61K 31/704* (2013.01); *A61K 45/06* (2013.01)

(58) Field of Classification Search
CPC .............. A61K 31/404; A61K 31/4706; A61K 31/4745
See application file for complete search history.

(56) References Cited

U.S. PATENT DOCUMENTS

| | | |
|---|---|---|
| 7,572,886 B2 | 8/2009 | Girard et al. |
| 9,044,474 B2 | 6/2015 | Byrd et al. |
| 9,873,670 B2 | 1/2018 | Watt et al. |
| 9,993,460 B2 | 6/2018 | Garner et al. |
| 10,512,641 B2 | 12/2019 | Rangnekar |
| 2013/0184330 A1 | 7/2013 | Lampidis et al. |
| 2017/0368072 A1 | 12/2017 | Malhotra et al. |
| 2018/0147197 A1 | 5/2018 | Rangnekar |
| 2019/0038601 A1 | 2/2019 | Bakewell et al. |
| 2019/0076431 A1 | 3/2019 | Lee et al. |
| 2021/0252032 A1 | 8/2021 | Rangnekar |
| 2022/0153805 A1 | 5/2022 | Zhan |

FOREIGN PATENT DOCUMENTS

| | | |
|---|---|---|
| CN | 102641508 A | 8/2012 |
| WO | WO2018235103 | 12/2018 |

OTHER PUBLICATIONS

Ji (Cancer Biology & Therapy 2014, 15, 570-577).*
Wang, et al., Neoadjuvant administration of hydroxychloroquine in a phase 1 clinical trial induced plasma Par-4 levels and apoptosis in diverse tumors, Genes & Cancer, vol. 9 (5-6), May 2018, pp. 190-197.
Zhang, et al., Inhibition of Bcl-2/Bcl-xL and c-MET causes synthetic lethality in model systems of glioblastoma, Scienific Reports, (2018) 8:7373, pp. 1-12.
Burikhanov, et al., Chloroquine-inducible Par-4 secretion is Essential for Tumor Cell Apoptosis and Inhibition of Metastasis, Cell Reports 18, 508-519, Jan. 10, 2017.
Lev, et al., Anti-pancreatic cancer activity of ONC212 involves the unfolded protein response (UPR) and is reduced by IGF1-R and GRP78/BIP, Oncotarget, 2017, vol. 8, (No. 47), pp. 81776-81793.
Rah, et al., PAWR-mediated suppression of BCL2 promotes switching of 3-azido withaferin A (3-AWA)-induced autophagy to apoptosis in prostate cancer cells, Autophagy 11:2, 314-331; Feb. 2015.
Raiter, et al., Pharmacological induction of cell surface GRP78 contributes to apoptosis in triple negative breast cancer cells, Oncotarget, vol. 5, No. 22, pp. 11452-11463.
Burikhanov, et al., Novel mechanism of apoptosis resistance in cancer mediated by extracellular PAR-4, Cancer Res; 73(2) Jan. 15, 2013, pp. 1011-1019.
Shrestha-Bhattarai, et al., Cancer-selective apoptotic effects of extracellular and intracellular Par-4, Oncogene (2010) 29, pp. 3873-3880.
Burikhanov, et al., The tumor suppressor Par-4 activates an extrinsic pathway for apoptosis, Cell 138, 377-388, Jul. 24, 2009.
Lee, et al., GRP78 as a novel predictor of responsiveness to chemotherapy in breast cancer, GRP78 as a Novel Predictor of Responsiveness to Chemotherapy in Breast Cancer, Cancer Res 2006; 66: (16).Aug. 15, 2006, pp. 7849-7853.
Wang, et al., Overexpression of endoplasmic reticulum molecular chaperone GRP94 and GRP78 in human lung cancer tissues and its significance, Cancer Detection and Prevention 29 (2005) 544-551.

(Continued)

*Primary Examiner* — Pancham Bakshi
(74) *Attorney, Agent, or Firm* — Stites & Harbison PLLC; Warren D. Schickli

(57) ABSTRACT

A method of treating cancer in an individual includes a step of administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual.

7 Claims, 3 Drawing Sheets

(56) References Cited

OTHER PUBLICATIONS

Burikhanov, et al., Paracrine Apoptotic Effect of p53 Mediated by Tumor Suppressor Par-4, Cell Reports 6, 1-7, Jan. 30, 2014.

Tsai, et al., Endoplasmic reticulum stress activates SRC, relocating chaperones to the cell surface where GRP78/CD109 blocks TGF-β signaling. Proc Natl Acad Sci USA. 2018.

Liston, et al., Clinically Relevant Concentrations of Anticancer Drugs: A Guide for Nonclinical Studies, Clin Cancer Res; 23(14) Jul. 15, 2017, pp. 3489-3498.

Mitou, et al., Targeting autophagy enhances the anti-tumoral action of crizotinib in ALK-positive anaplastic large cell lymphoma, Oncotarget, vol. 6, No. 30, pp. 30149-30164.

Santos, et al., Potential Therapeutic Agents Against Par-4 Target for Cancer Treatment: Where Are We Going?, Current Drug Targets, 2019, 20, 5, pp. 1-20.

You, et al., Crizotinib induces autophagy through inhibition of the STAT3 pathway in multiple lung cancer cell lines, Oncotarget, vol. 6, No. 37, pp. 40268-40282.

Arap, et al., Cell surface expression of the stress response chaperone GRP78 enables tumor targeting by circulating ligands, Cancer Cell, 2004, vol. 6, pp. 275-284.

Araujo, et al., GRP78 Is a Targetable Receptor on Cancer and Stromal Cells, EBioMedicine, 33 (2018), 2-3.

Burikhanov, et al., Arylquins target vimentin to trigger Par-4 secretion of tumor cell apoptosis, Nat Chem Biol 2014, 10, 924-926.

Crizotinib, Prescribing Information, 2017, 28 pages (Year: 2017).

Chloroquine phosphate, Prescribing information, 2017, 10 pages (Year: 2017).

Hydroxychloroquine sulfate. Prescribing information, revised Jan. 2017, 11 pages (Year: 2017).

Ji, et al., Induction of autophagy contributes to crizotinib resistance in AL-positive lung cancer; Cancer Biology & Therapy, vol. 15, Issue 5, pp. 570-577.

Liu, et al., Crizotinib—a tyrosine kinase inhibitor that stimulates immunogenic cell death, Oncoimmunology, 2019, vol. 8, No. 7, pp. 1-3.

Rebecca, et al., Emergin strategies to effectively target autophagy in cancer, Oncogene (2016) 35, pp. 1-11.

Schwarze, et al., Targeting plasma membrane GRP78 for cancer growth inhibition, Cancer Biology & Therapy, 2010, pp. 153-155.

Sviripa, et al., Par-4 secretion: stoichiometry of 3-arylquinoline, Organic & Biomolecular Chemistry, 2016, 14, pp. 74-84.

Zhou, et al., The multi-targeted tyrosine kinase inhibitor vandetanib plays a bifunctional role in non-small cell lung cancer cells, Scientic Reports, 5 :8629, 2015, pp. 1-10.

\* cited by examiner

US 11,730,750 B2

DRUGS FOR GRP78 CELL SURFACE TRANSLOCATION AND PAR-4 SECRETION

RELATED APPLICATION

This application claims priority to U.S. Provisional Patent Application Ser. No. 62/977,582 filed on Feb. 17, 2020 which is hereby incorporated by reference in its entirety.

TECHNICAL FIELD

This document relates generally to the field of oncology and to a new and improved method for treating cancer including, particularly, lung cancer in its various forms including treatment resistant lung cancers.

BACKGROUND

Prostate apoptosis response-4 (Par-4, also known as PAWR) is a protein secreted by normal cells that induces paracrine apoptosis in cancer cells by binding to cell surface GRP78 receptor that is present mainly on the surface of cancer cells. Therefore, secreted Par-4 kills mainly cancer cells, not normal cells. Our previous studies have identified FDA-approved anti-malarial drugs as robust secretagogues of Par-4 protein in cell culture, mouse models, and in human individuals in clinical trials. Moreover, we identified Crizotinib (CZT), which is an inhibitor of ALK/MET/ROS1 kinases, as an inducer of Par-4 receptor GRP78 levels on lung cancer cells. In conjunction with CZT, CQ induced significantly greater inhibition of LLC1-derived lung tumor nodules, relative to that with CZT or CQ administered separately.

This document relates to new and improved methods of treating cancer, including lung cancer, in an individual including a human individual and other mammals.

SUMMARY

In accordance with the purposes and benefits described herein, a new and improved method of treating cancer uses novel and effective synergistic drug combinations. More particularly, this involves a combination of drugs including a first drug or active agent that induces the secretion of Par-4 from normal cells and a second drug or active agent that induces or elevates the Par-4 receptor GRP78 on the cancer cell surface. The method of treating cancer in an individual or patient comprises the step of administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual.

In other embodiments, the new and improved method consists essentially of the step of administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual.

In one or more of the many possible embodiments of the method, the method includes selecting the first active agent from a first group of agents consisting of chloroquine, hydroxychloroquine, a p53-activating agent, etoposide, doxorubicin, irinotecan and combinations thereof.

In one or more of the many possible embodiments of the method, the method includes selecting the second active agent from a second group of agents consisting of an ALK-inhibitor, a surviving inhibitor, an EGFR inhibitor, an aurora kinase inhibitor, crizotinib, brigatinib, YM155, afatinib, alisertib and combinations thereof.

In one or more of the many possible embodiments of the method, the first active agent and the second active agent are administered at least once a day for at least 30-180 days. In one or more of the many possible embodiments of the method, the first active agent and the second active agent are administered in a combined synergistic amount.

In the following description, there are shown and described several preferred embodiments of the method. As it should be realized, the method is capable of other, different embodiments and its several details are capable of modification in various, obvious aspects all without departing from the method as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the patent specification, illustrate several aspects of the method and together with the description serve to explain certain principles thereof.

Reference will now be made in detail to the present preferred embodiments of the method, examples of which are illustrated in the accompanying drawing figures.

DETAILED DESCRIPTION

The new and improved method of treating cancer in an individual may be broadly described as including the step of administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual.

This synergistic combination of active agents is even effective to overcome therapy resistance in lung cancer, which remains the leading cause of cancer mortality in the United States. The tumor suppressor Par-4 inhibits the growth of both chemotherapy-sensitive and chemotherapy-resistant cancer cells. Par-4 protein binds to the receptor GRP78 found on the surface of cancer cells and induces apoptosis of the cancer cells by caspase-8/caspase-3 activation.

While basal levels of Par-4 secreted from normal cells are inadequate to induce robust apoptosis of cancer cells, the first active agent promotes Par-4 secretion to levels that provide effective cancer treatment. p53-inducing FDA-approved drugs, such as etoposide, doxorubicin, and irinotecan trigger Par-4 secretion from normal cells at levels comparable to, or higher than, those achieved previously with chloroquine.

Figure 1:
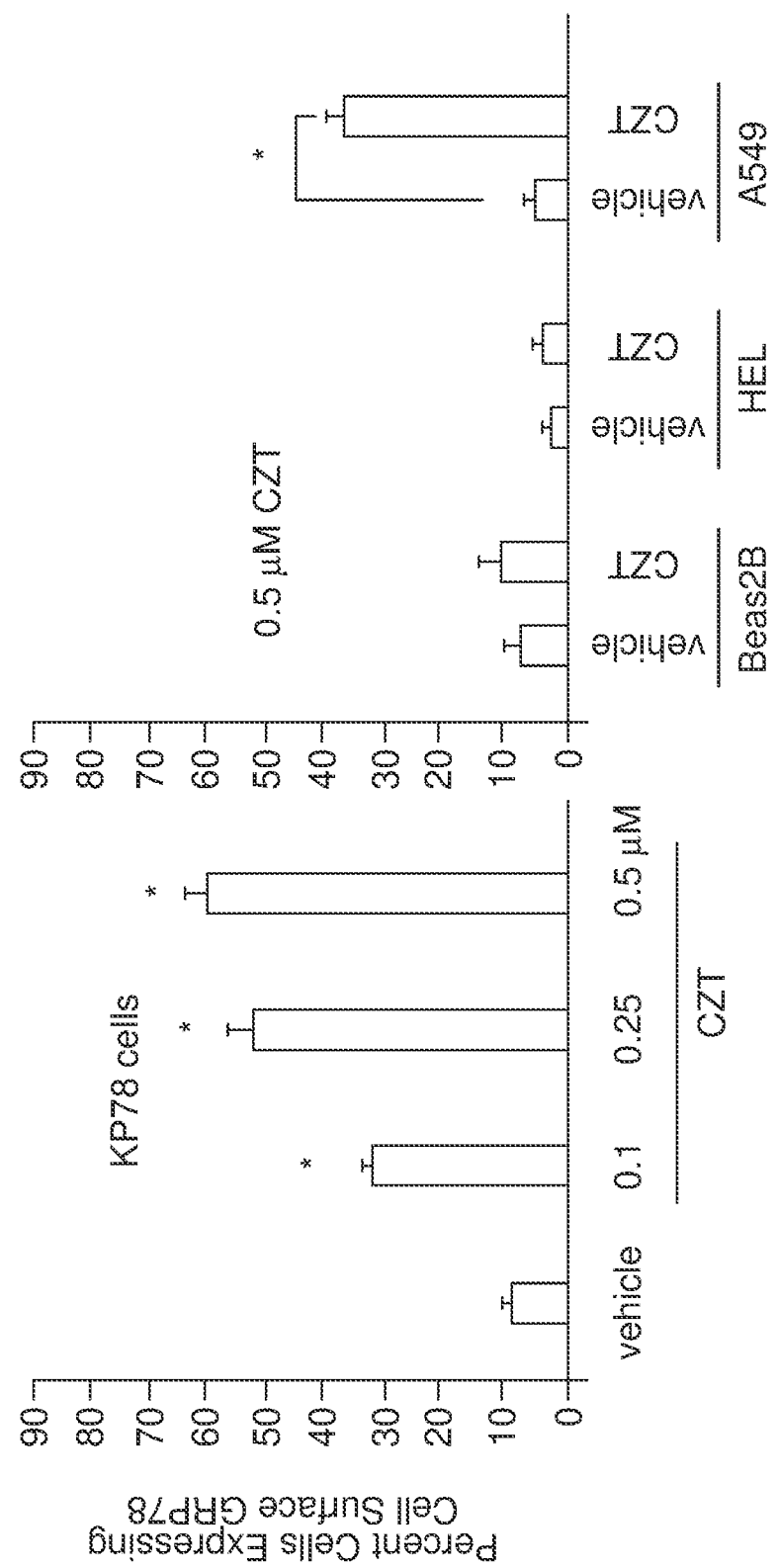
FIG. 1 is a graph illustrating how CTZ induces cell surface expression of GRP78 in cancer cells but not normal cells.
Figure 2:
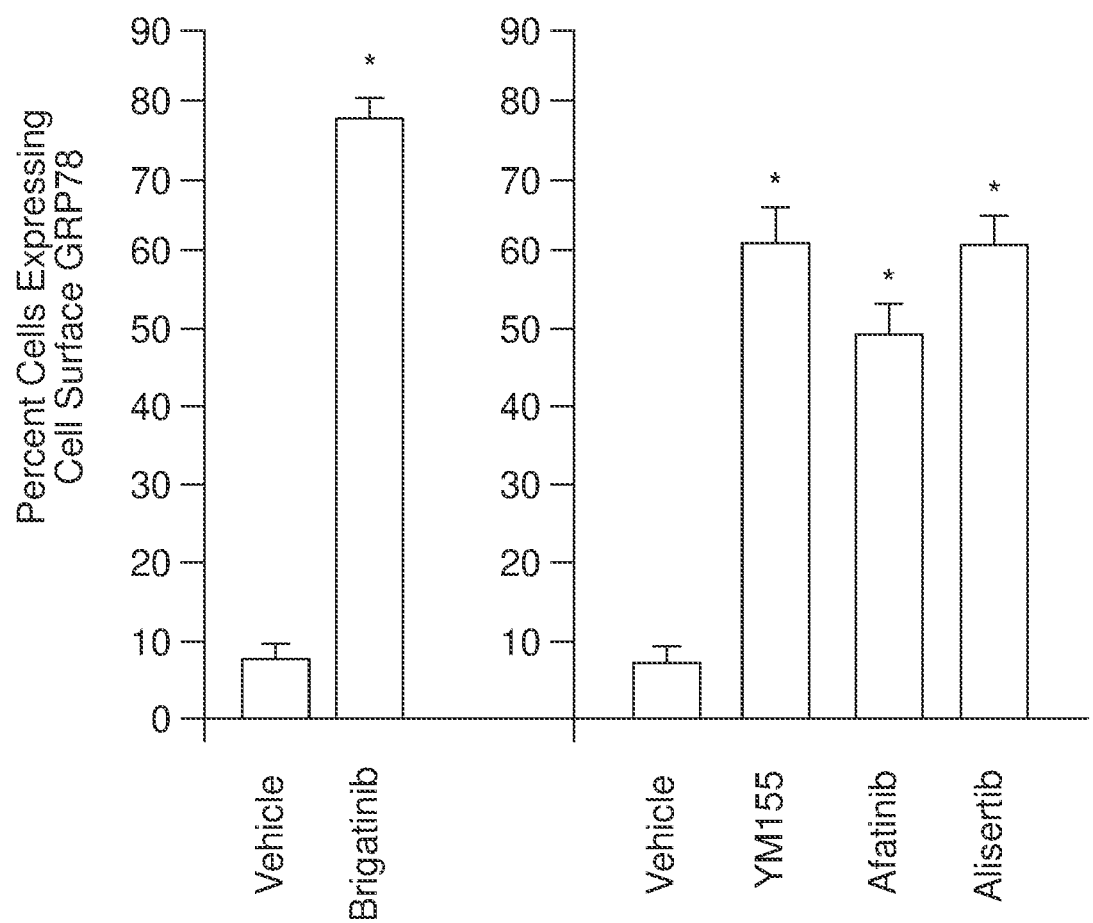
FIG. 2 is a graph illustrating how brigatinib, YM155, afatinib and alisertib induce cell surface expression of GRP78 in cancer cells.

To maximize the apoptotic effect of secreted Par-4 on lung tumors, the second active agent is effective to elevate GRP78 on the surface of cancer cells and thereby complements the apoptotic action of secreted Par-4. Crizotinib (CZT), an inhibitor of anaplastic lymphoma kinase (ALK), is useful as the second active agent. Approximately 5% of patients with non-small cell lung cancer (NSCLC) have tumors that contain an inversion in chromosome 2 that juxtaposes the 5' end of the echinoderm microtubule-associated protein-like 4 (EML4) gene with the 3' end of the ALK gene. This juxtaposition results in the fusion oncogene called EML4-ALK. ALK+ tumors are highly sensitive to therapy with ALKtargeted inhibitors. Moreover, CZT also targets NSCLC with MET/ROS1 kinase activation. Patients with ALK, MET and ROS1 rearrangements that are prognostic and predictive biomarkers in NSCLC initially respond to CZT, but many of these patients relapse with CZT-resistant tumors. CZT elevated the Par-4 receptor GRP78 on the surface of ALK-negative A549 and p53-deficient KP7B lung tumor cells but not in normal lung fibroblast HEL cells or epithelial BEAS2B cells (See FIG. 1). We determined that in addition to CZT, nanomolar concentrations of YM155 (survivin inhibitor), afatinib (EGFR inhibitor), and alisertib (aurora kinase inhibitor), and/or another ALK-inhibitor brigatinib, induced GRP78 cell surface translocation in lung cancer cells (See FIG. 2). Recent studies indicated that GRP78 translocation to the cell surface is associated with the activation of the proto-oncogene, tyrosine-protein kinase SRC. On the other hand, phosphorylation of SRC at tyrosine 530 (Y530) by C-terminal SRC kinase (Csk) and Csk homologous kinase results in inactivation of SRC.

Figure 3:
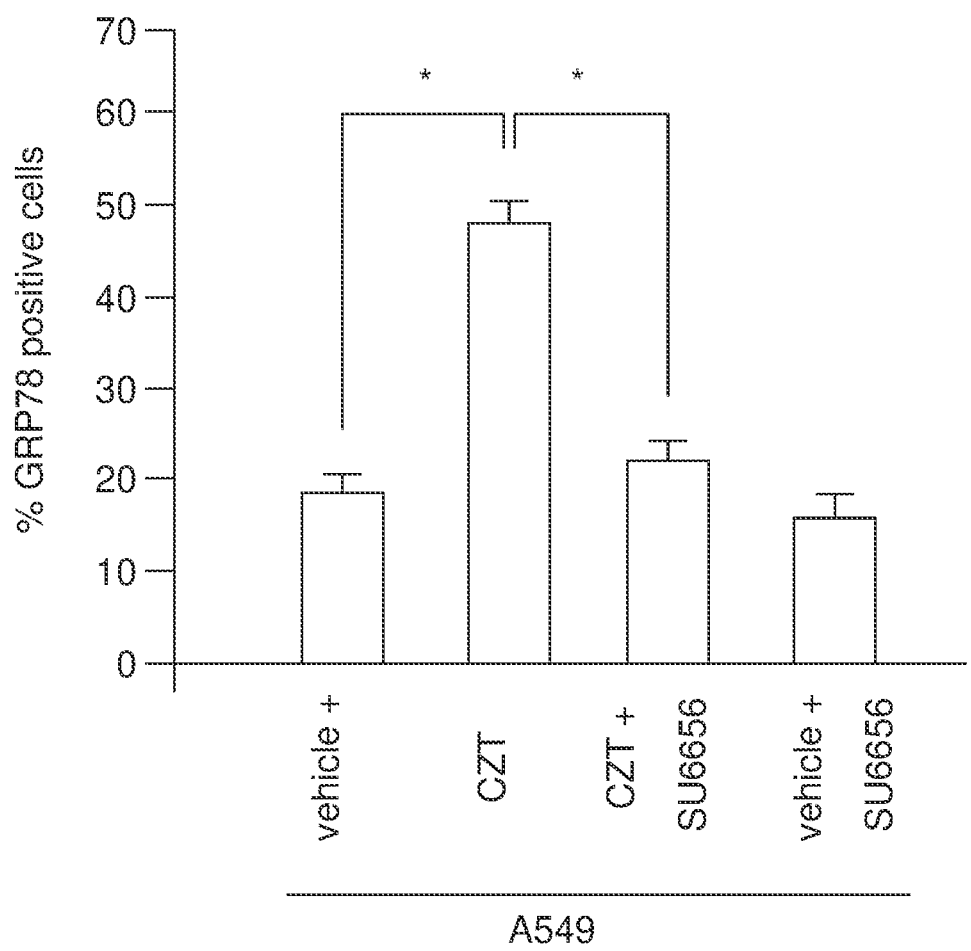
FIG. 3 is a graph illustrating how cell surface transport of GRP78 is SRC kinase-dependent.

Dephosphorylation of Y530 by phosphatases results in autophosphorylation of SRC at Y419, leading to activation. SRC activation triggers a signaling cascade that prevents retrograde trafficking of proteins from the Golgi to the ER and promotes GRP78 translocation from the Golgi to the cell surface. Interestingly, our studies indicated that CZT and other ALK-inhibitors such as brigatinib, alectinib and lorlatinib cause the activation of SRC, and SRC activation is essential for translocation of GRP78 to the lung cancer cell surface (FIG. 3). Because SRC activation results in treatment resistance to ALK-tyrosine kinase inhibitors, our synergistic combination of first and second active agents usurps the tumor resistance pathway and induces cell-surface GRP78-dependent apoptosis by Par-4 secreted from normal cells in response to p53-inducing drugs.

The first active agent and the second active agent may be administered in a combined formulation or in separate formulations in any order or simultaneously. The first active agent and the second active agent may be administered by known means and at dosage rates known to be useful for the intended purpose of treating cancer. For example, the first active agent and the second active agent may be administered in a combined synergistic amount for at least once a day for at least 30-180 days.

Various known drugs may be used as the first active agent including chloroquine, hydroxychloroquine, a p53-activating agent, etoposide, doxorubicin, irinotecan and combinations thereof.

P53-activating agents include, but are not necessarily limited to, doxorubicin, etoposide, Nutlin, irinotecan, chloroquine, hydroxychloroquine and combinations thereof.

Various known drugs may be used as the second active agent including an ALK-inhibitor, a survivin inhibitor, an EGFR inhibitor, an aurora kinase inhibitor, crizotinib, brigatinib, YM155, afatinib, alisertib and combinations thereof.

ALK-inhibitors include, but are not necessarily limited to, crizotinib, brigatinib, lorlatinib, alectinib and combinations thereof.

Survivin inhibitors include, but are not necessarily limited to, YM155.

EGFR inhibitors include, but are not necessarily limited to, afatinib, gefitinib, erlotinib, osimertinib and combinations thereof.

Aurora kinase inhibitors include, but are not necessarily limited to, alisertib, barasertib, danusertib, AT9283, PF-03814735, AMG 900 and combinations thereof.

The first and second active agents specifically identified above may be administered in known forms at known dosage rates. Orally administered first and second agents may be administered as pills, capsules and liquid emulsions in accordance with state-of-the-art practice. Other first and second agents may be administered intravenously by IV or injection as is known in the art.

For example, crizotinib may be administered orally at a dosage rate of 200-250 mg/day. In some embodiments of the method, crizotinib is administered twice a day: that is, a 200 mg dose in the AM and a 200 mg dose in the PM.

Brigatinib may be administered orally at a dosage of between 30-180 mg/day and, more particularly, 90 mg/day.

Afatinib may be administered orally at a dosage rate of 20-40 mg/day.

Alectinib may be administered orally at a dosage rate of between 300-600 mg/day and typically about 450 mg/day.

Lorlatinib may be administered orally at a dosage rate of between 20-100 mg/day. In at least one embodiment of the method, lorlatinib is administered orally at a rate of 75 mg twice daily.

Etoposide may be administered by IV at a dosage rate of between 20-100 $mg/mm^2$ with a 30-60 minute decreasing dose.

Irinotecan may be administered by IV at a dosage rate of 125-300 $mg/mm^2$ and typically at a dosage rate of 180 $mg/mm^2$.

Doxorubicin may be administered by IV at a dosage rate of 60-100 $mg/mm^2$.

Single or multiple administrations of the first and second active agents are possible depending upon the dosage and frequency as required to provide pharmaceutically effective treatment and as tolerated by the individual/patient.

In summary, the new and improved method include administering to an individual a first active agent that induces the secretion of Par-4 from normal cells that synergizes with a second active agent that upregulates Par-4 receptors (GRP78) on cancer cells. This new and improved method expands the range of action of these diverse drugs beyond tumors expressing activated ALK/MET/ROS1, survivin, EGFR, or aurora kinase. Accordingly, the new p53-activating drug+GRP78 translocator drug combination should be clinically effective against a broad range of tumors that are resistant to p53-inducers or ALK-inhibitors acting alone, as well as in most lung tumors that lack activated ALK.

Each of the following terms written in singular grammatical form: "a", "an", and the", as used herein, means "at least one", or "one or more". Use of the phrase "One or more" herein does not alter this intended meaning of "a", "an", or "the". Accordingly, the terms "a", "an", and "the", as used herein, may also refer to, and encompass, a plurality of the stated entity or object, unless otherwise specifically defined or stated herein, or, unless the context clearly dictates otherwise.

Each of the following terms: "includes", "including", "has", "having", "comprises", and "comprising", and, their linguistic/grammatical variants, derivatives, or/and conjugates, as used herein, means "including, but not limited to", and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The phrase "consisting essentially of" means that the stated method, which is an entirety or part of an exemplary embodiment of the disclosed invention, or/and which is used for implementing an exemplary embodiment of the disclosed invention, may include at least one additional feature or characteristic, but only if each such additional feature or characteristic does not materially alter the basic novel and inventive characteristics or special technical features, of the claimed item: that is, the synergistic effect described herein.

The term "method", as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Terms of approximation, such as the terms about, substantially, approximately, etc., as used herein, refers to ±10% of the stated numerical value. Use of the terms parallel or perpendicular are meant to mean approximately meeting this condition, unless otherwise specified.

It is to be fully understood that certain aspects, characteristics, and features, of the method of treating cancer in an individual, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the method which are illustratively described and presented in combination or sub-combination in the context or format of a single embodiment may also be illustratively described and presented in the context or format of a plurality of separate embodiments.

Although the method has been illustratively described and presented by way of specific exemplary embodiments, it is evident that many alternatives, modifications, or/and variations, thereof, will be apparent to those skilled in the art. The method described above and in the following claims may also be accurately expressed as "consisting of" rather than "comprising" or "consisting essentially of" the step or steps indicated in the body of the following claims. Accordingly, it is intended that all such alternatives, modifications, or/and variations, fall within the spirit of, and are encompassed by, the broad scope of the appended claims.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A method of treating lung cancer in an individual, comprising: administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual wherein the the first active agent is selected from a first group of agents consisting of chloroquine, hydroxychloroquine, etoposide, doxorubicin, Nutlin, irinotecan and combinations thereof and the second active agent is selected from a second group of agents consisting of crizotinib, brigatinib, lorlatinib, alectinib, sepantronium bromide (YM155), afatinib, gefitinib, erlotinib, osimertinib, alisertib, barasertib, danusertib, 1-Cyclopropyl-3-[3-(5-morpholin-4-ylmethyl-1H-benzoimidazol-2-yl)-1H-pyrazol-4-yl]-urea (AT9283), N-(2-((1S,4R)-6-((4-(Cyclobutylamino)-5-(trifluoromethyl)pyrimidin-2-yl)amino)-1,2,3,4-tetrahydro-1,4-epiminonaphthalen-9-yl)-2-oxoethyl)acetamide (PF-03814735), N-[4-[3-(2-aminopyrimidin-4-yl)pyridin-2-yl]oxyphenyl]-4-(4-methylthiophen-2-yl)phthalazin-1-amine (AMG900) and combinations thereof and the second active agent is administered at a dosage rate of 400 mg/day.

2. The method of claim 1, wherein the first active agent and the second active agent are administered in a combined synergistic amount.

3. The method of claim 1, wherein the first active agent and the second active agent are administered at least once a day for at least 30-180 days.

4. A method of treating lung cancer in an individual, consisting essentially of: administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual wherein the first active agent is selected from a first group of agents consisting of chloroquine, hydroxychloroquine, etoposide, doxorubicin, Nutlin, irinotecan and combinations thereof and the second active agent is selected from a second group of agents consisting of crizotinib, brigatinib, lorlatinib, alectinib, YM155, afatinib, gefitinib, erlotinib, osimertinib, alisertib, barasertib, danusertib, AT9283, PF-03814735, AMG 900 and combinations thereof and the second active agent is administered at a dosage rate of 400 mg/day.

5. The method of claim 4, wherein the first active agent and the second active agent are administered at least once a day for at least 30-180 days.

6. A method of treating lung cancer in an individual, consisting of: administering to the individual a pharmaceutically effective amount of (a) a first active agent adapted for producing secretion of prostate apoptosis response-4 (Par-4) from normal cells and (b) a second active agent adapted for elevating GRP78 receptors for Par-4 on a surface of a cancer cell in the individual wherein the first active agent is selected from a first group of agents consisting of chloroquine, hydroxychloroquine, etoposide, doxorubicin, Nutlin, irinotecan and combinations thereof and the second active agent is selected from a second group of agents consisting of crizotinib, brigatinib, lorlatinib, alectinib, YM155, afatinib, gefitinib, erlotinib, osimertinib, alisertib, barasertib, danusertib, AT9283, PF-03814735, AMG 900 and combinations thereof and the second active agent is administered at a dosage rate of 400 mg/day.

7. The method of claim 6, wherein the first active agent and the second active agent are administered at least once a day for at least 30-180 days.

* * * * *

UNITED STATES PATENT AND TRADEMARK OFFICE
CERTIFICATE OF CORRECTION

| | |
|---|---|
| PATENT NO. | : 11,730,750 B2 |
| APPLICATION NO. | : 17/178096 |
| DATED | : August 22, 2023 |
| INVENTOR(S) | : Vivek M. Rangnekar et al. |

It is certified that error appears in the above-identified patent and that said Letters Patent is hereby corrected as shown below:

In the Specification

Column 1, Line 16, insert the following:
--Government Support
This invention was made with government support under Grant Nos. CA187273, CA 165990, and CA177558, awarded by the National Institutes of Health. The government has certain rights in the invention.--

Signed and Sealed this
Twenty-fourth Day of October, 2023

Katherine Kelly Vidal
*Director of the United States Patent and Trademark Office*